United States Patent
Yamamoto et al.

(10) Patent No.: US 8,556,624 B2
(45) Date of Patent: Oct. 15, 2013

(54) ORTHODONTIC APPLIANCE

(75) Inventors: Teruko Yamamoto, Okayama (JP); Hiroshi Kamioka, Kurashiki (JP); Taiji Adachi, Kyoto (JP); Shogo Fukushima, Moriguchi (JP); Takumi Sakimura, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/961,764

(22) Filed: Dec. 7, 2010

(65) Prior Publication Data

US 2011/0076634 A1    Mar. 31, 2011

Related U.S. Application Data

(63) Continuation of application No. 11/813,375, filed as application No. PCT/JP2007/058043 on Apr. 12, 2007, now Pat. No. 8,123,520.

(30) Foreign Application Priority Data

Nov. 27, 2006   (JP) ................................. 2006-318007

(51) Int. Cl.
*A61C 3/00*   (2006.01)

(52) U.S. Cl.
USPC ......................................................... 433/18

(58) Field of Classification Search
USPC .......... 433/18–21, 37, 41–48; 601/46, 48, 70, 601/72, 73, 78, 80, 97, 101, 108, 110
See application file for complete search history.

(56) References Cited

U.S. PATENT DOCUMENTS

| | | | | |
|---|---|---|---|---|
| 3,332,150 A | * | 7/1967 | Mumaw | 433/24 |
| 4,123,844 A | * | 11/1978 | Kurz | 433/5 |
| 4,229,165 A | | 10/1980 | Kurz | |
| 4,244,688 A | | 1/1981 | Kurz | |
| 4,348,177 A | | 9/1982 | Kurz | |
| 4,348,178 A | * | 9/1982 | Kurz | 433/6 |
| 4,382,780 A | * | 5/1983 | Kurz | 433/5 |
| 4,511,330 A | | 4/1985 | Smiley et al. | |
| 5,334,015 A | | 8/1994 | Blechman | |
| 5,967,784 A | | 10/1999 | Powers | |
| 5,975,893 A | | 11/1999 | Chishiti et al. | |
| 6,183,248 B1 | | 2/2001 | Chishiti et al. | |

(Continued)

FOREIGN PATENT DOCUMENTS

| | | |
|---|---|---|
| DE | 4020647 | 1/1992 |
| JP | 4-46585 | 7/1992 |

(Continued)

OTHER PUBLICATIONS

Shimizu, "A study of the movement of the lateral incisor of the *Macaca fuscata* loaded by a vibrating force," Journal of Japan Orthodontic Society, 45, pp. 56-72, 1986 (including an English language Abstract).

(Continued)

*Primary Examiner* — Robyn Doan
*Assistant Examiner* — Matthew Nelson
(74) *Attorney, Agent, or Firm* — Greenblum & Bernstein P.L.C.

(57) ABSTRACT

The present invention provides an orthodontic appliance having a load applying mechanism. To correct malocclusion, the load applying mechanism may include a projection fixed to the specified tooth in the teeth so as to project from the specified tooth in the teeth.

1 Claim, 7 Drawing Sheets

(56) References Cited

U.S. PATENT DOCUMENTS

| | | | |
|---|---|---|---|
| 6,210,162 | B1 | 4/2001 | Chishiti et al. |
| 6,217,325 | B1 | 4/2001 | Chishiti et al. |
| 6,227,850 | B1 | 5/2001 | Chishiti et al. |
| 6,227,851 | B1 | 5/2001 | Chishiti et al. |
| 6,299,440 | B1 | 10/2001 | Phan et al. |
| 6,309,215 | B1 | 10/2001 | Phan et al. |
| 6,390,812 | B1 | 5/2002 | Chishiti et al. |
| 6,471,511 | B1 | 10/2002 | Chishiti et al. |
| 6,633,747 | B1 | 10/2003 | Reiss |
| 7,163,399 | B2 | 1/2007 | Kajimoto et al. |
| 2002/0051951 | A1* | 5/2002 | Chishti et al. ............... 433/6 |
| 2004/0013993 | A1 | 1/2004 | Ito |
| 2004/0058295 | A1 | 3/2004 | Bergersen |
| 2004/0209218 | A1 | 10/2004 | Chishiti et al. |
| 2007/0065768 | A1 | 3/2007 | Naday |
| 2009/0061375 | A1 | 3/2009 | Yamamoto et al. |
| 2009/0061379 | A1 | 3/2009 | Yamamoto et al. |
| 2009/0061380 | A1 | 3/2009 | Yamamoto et al. |

FOREIGN PATENT DOCUMENTS

| | | |
|---|---|---|
| JP | 11-155273 | 6/1999 |
| JP | 2001-340412 | 12/2001 |
| JP | 2002-102255 | 4/2002 |
| JP | 2003-290250 | 10/2003 |
| JP | 2004-113625 | 4/2004 |
| JP | 2004-201895 | 7/2004 |
| WO | 00/19928 | 4/2000 |
| WO | 02/073185 | 9/2002 |
| WO | 2005/092234 | 10/2005 |
| WO | WO 2005092234 A1 * 10/2005 ............... A61C 7/08 |  |

OTHER PUBLICATIONS

Ohmae et al., "Biomechanical acceleration of experimental tooth movement by ultrasonic vibration in vivo: Part 1, Homo-directional application of ultrasonication to orthodontic force," Journal of Japan Orthodontic Society, Orthod. Wave, 60(4), pp. 201-212, 2001 (including an English language Abstract).

Chiba et al., "Effects of Mechanical stimulation using resonance vibration on the periodontium" (including an English language Abstract), 2009.

Emata, "The mechanical response of the periodontal structure in the maxillary lateral incisor of the *Macaca fuscata* yakui, loading by a vibrating force," Japanese Journal of Oral Bial., 21:571-585, 1979 (including an English language Abstract).

\* cited by examiner

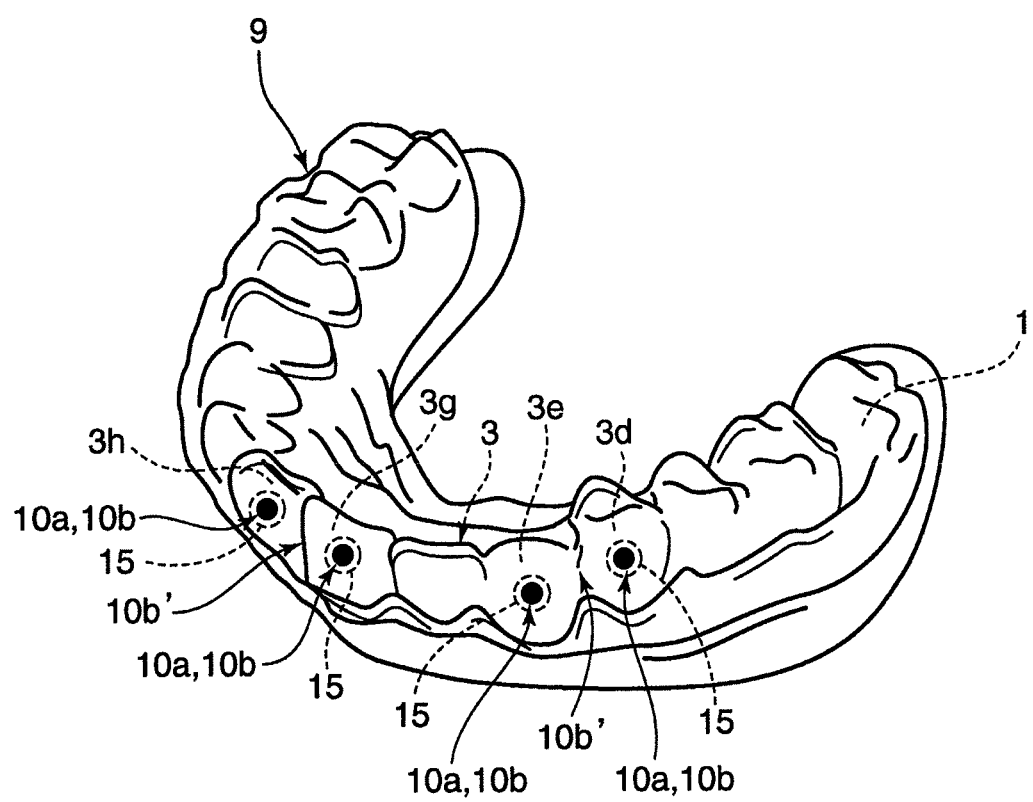

ORTHODONTIC APPLIANCE

CROSS-REFERENCE TO RELATED APPLICATION

The present application is a continuation of U.S. application Ser. No. 11/813,375, filed Jul. 5, 2007, which is a National Stage Application of PCT/JP2007/58043, filed Apr. 12, 2007, the disclosures of which incorporated herein by reference in their entireties.

TECHNICAL FIELD

The present invention relates to an orthodontic appliance.

BACKGROUND ART

An orthodontic appliance equipped with an orthodontic wire to be mounted on teeth has been conventionally known. An elastic restoring force of the orthodontic wire acts as a constant static load on the teeth to correct teeth malalignment or crossbite. In other words, the orthodontic appliance is based on the principle of aligning the teeth by gradually deforming an alveolar bone supporting the teeth in the gum (bone reconstruction, bone remodeling) through the application of a constant force to the teeth.

However, the teeth alignment using the orthodontic wire takes a very long time (fastest six months, normally several years) until an orthodontic treatment is finished. Such a long treatment period increases burdens on patients, causing them to give up easily.

In order to shorten a period of such an orthodontic treatment, technology of giving a vibration force to the teeth has been studied. For example, a study result to the effect that if a sample A in which a constant force was applied to the teeth and a sample B in which a vibration force was applied to the teeth are compared, the sample B in which the vibration force was applied is more effective in shortening the period as shown in FIG. 7A is disclosed in Non-Patent Literature 1. Similarly, a study result to the effect that if a sample C in which a constant force was applied to the teeth and a sample D in which a constant force and a vibration force were applied to the teeth are compared, the sample D in which the constant force and vibration force were applied is more effective in shortening the period as shown in FIG. 7B is disclosed in non-Patent Literature 2.

According to these studies, the application of the vibration force to the teeth remarkably shortens the period of orthodontic treatment to about ½ to ⅓ as compared to conventional technologies. Further, it is sufficient to apply a vibration force only for 1.5 hours a day according to the former literature and only for 2 minutes at a time and once every two weeks according to the latter literature.

It can be understood from these studies that the teeth alignment by applying a vibration force as well as a constant force to the teeth is more effective in remarkably shortening the period of orthodontic treatment than the teeth alignment only by applying a constant force to the teeth using an orthodontic wire or the like.

Appliances for putting the above studies to practical use have been conventionally proposed. Specifically, Patent Literature 1 discloses an appliance provided with a dental mouthpiece to be mounted on teeth to urge movements of teeth to be aligned and means for applying ultrasonic vibration to tissues surrounding the mounted position of the dental mouthpiece. Further, Patent Literature 2 discloses an appliance for applying ultrasonic vibration to teeth to be aligned.

However, the appliances disclosed in the above Patent Literatures 1, 2 have a problem that ultrasonic vibration cannot be efficiently applied to the teeth to be aligned since both of them receive the application of ultrasonic vibration from the outside, for example, by pressing an ultrasonic head against the cheek skin. Further, since the respective appliances require an ultrasonic generator, there is also a problem that treatment cannot be continued unless a patient goes to a dental clinic equipped with these appliances.

[Non-Patent Literature 1] Shimizu: "Journal of Japan Orthodontic Society" 45, pp. 56-72, 1986

[Non-Patent Literature 2] Ohmae et al.: "Journal of Japan Orthodontic Society" 60(4), p. 201, 2001

[Patent Literature 1] Japanese Unexamined Patent Publication No. 2002-102255

[Patent Literature 2] Japanese Unexamined Patent Publication No. 2004-201895

DISCLOSURE OF THE INVENTION

In order to solve the above problems, an object of the present invention is to provide an orthodontic appliance capable of efficiently applying vibration to teeth to be aligned and enabling a treatment to be easily and safely continued even at home.

In order to accomplish the above object, an orthodontic appliance according to the present invention comprises a load applying mechanism and a vibration generating actuator. The load applying mechanism is mounted on teeth to apply a load for teeth alignment to a specified tooth in the teeth. The vibration generating actuator includes a contact portion that is inserted into a buccal cavity containing the teeth from the outside and can come into contact with a part of the load applying mechanism corresponding to the specified tooth or the specified tooth, and applies a vibration force from the contact portion to the specified tooth or the part of the load applying mechanism corresponding to the specified tooth. Accordingly, this vibration generating actuator can efficiently apply the vibration force to the specified tooth or the part of the load applying mechanism corresponding to the specified tooth, thereby remarkably shortening a period required for teeth alignment.

BRIEF DESCRIPTION OF THE DRAWINGS

FIG. 4 is a perspective view of a dental cast of a lower dental arch where a dental mouthpiece as a load applying mechanism according to a second embodiment of the invention is mounted on teeth.

BEST MODES FOR EMBODYING THE INVENTION

Hereinafter, best modes for embodying the present invention are described in detail with reference to the accompanying drawings.

Figure 1:
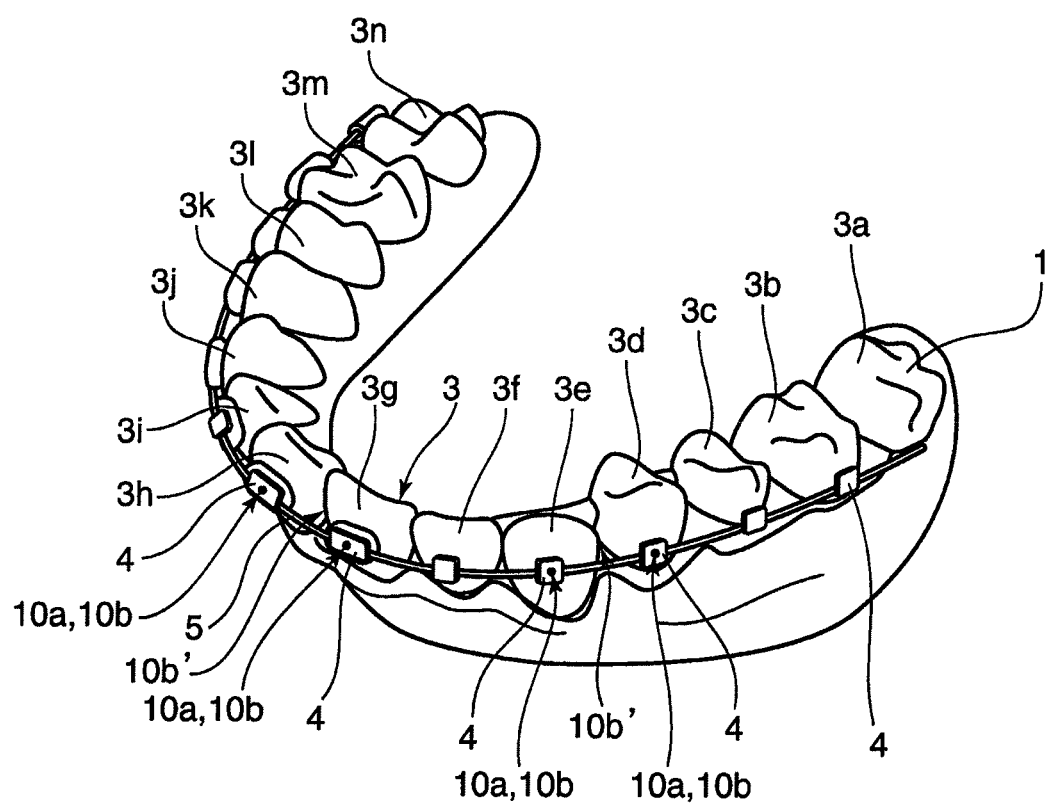
FIG. 1 is a perspective view of a dental cast of a lower dental arch where a mechanism including an orthodontic wire and brackets as a load applying mechanism according to a first embodiment of the invention is mounted on teeth.

FIG. 1 is a perspective view of a dental cast 1 of a lower dental arch according to a first embodiment of the present invention. This dental cast 1 has a teeth group 3 that includes a plurality of teeth 3a to 3n, wherein the teeth 3a, 3n are posterior teeth. A load applying mechanism for teeth alignment is mounted on the teeth 3b to 3m excluding these posterior teeth.

This load applying mechanism includes a plurality of brackets 4 to be fixed to the buccal surfaces of the teeth 3b to 3m and an orthodontic wire (arch wire) 5 arranged to connect these brackets 4. This orthodontic wire 5 is latched to the teeth 3b to 3m by the respective brackets 4. The orthodontic wire 5 is elastically deformably latched, so that an elastic restoring force thereof acts as a constant static load on the teeth group 3. The application of this static load corrects malocclusion. It should be noted that the load applying mechanism for aligning the teeth is not limited to the one shown in FIG. 1.

An orthodontic appliance according to this embodiment is provided with a vibration generating actuator 8 in addition to the above load applying mechanism. Examples of the vibration generating actuator 8 are shown in FIGS. 2A and 2B.

Figure 2A:
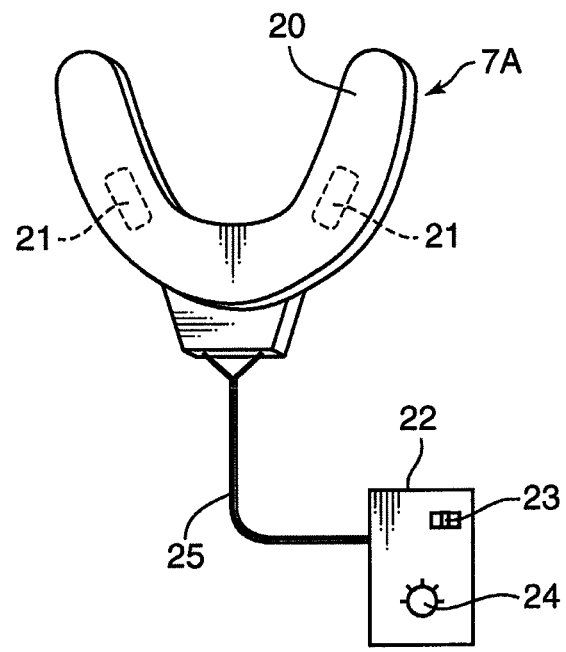
FIGS. 2A and 2B are perspective views showing examples of a vibration generating actuator.

FIG. 2A shows a bite board 7A as the vibration generating actuator. This bite board 7A includes a main body 20 to be chewed by the upper and lower teeth of a user (patient), vibrating elements 21 built in this main body 20, and a control box 22 electrically connected to the vibrating element 21s via cables 25. The vibrating elements 21 vibrate upon receiving the power supply and transmit this vibration to the teeth. The control box 22 has a switch 23 and a volume knob 24 and controls the frequency of the vibration generated by the vibrating elements 21 according to an operated amount of this volume knob 24.

The main body 20 of this bite board 7A is inserted into the buccal cavity from the outside, and brought into contact with the teeth 3d, 3e, 3g and 3h to be aligned, to which constant aligning forces are applied from the brackets 4 and the orthodontic wire 5, by being chewed by the upper and lower teeth. This contact enables the bite board 7A to efficiently apply vibration to the teeth 3d, 3e, 3g and 3h to be aligned. The application of such vibration remarkably shortens a period required for teeth alignment.

Figure 2B:
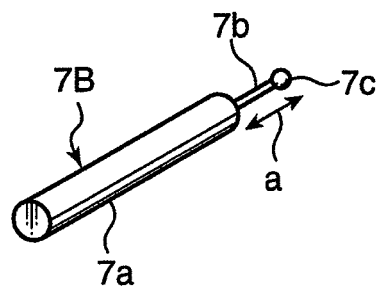

On the other hand, FIG. 2B shows a vibration generating probe 7B as the vibration generating actuator. This vibration generating probe 7B includes a main body 7a extending in one direction, a shaft 7b extending from this main body 7a along the central axis of the main body 7a, and a ball-shaped vibrating element 7c disposed at the tip of the shaft 7b, and the shaft 7b and the ball-shaped vibrating element 7c vibrate in axial directions (directions of arrows "a" in FIG. 2B) as power is supplied to the main body 20. For example, a vibration generating probe used in a vibration-type household electric toothbrush or electric shaver can be used as the vibration generating probe 7B.

In the above load applying mechanism, markings (colored markers) 10a are applied as positioning portions to the brackets 4 corresponding to specified teeth (e.g. teeth 3d, 3e, 3g and 3h to be aligned) of the teeth group 3 shown in FIG. 1. These markings 10a may be applied to the orthodontic wire 5 or markings may be applied to the teeth 3d, 3e, 3g and 3h to be aligned themselves.

The positioning portions according to the present invention are not limited to the markings 10a. For example, as shown in FIG. 1, dents 10b as the positioning portions may be formed in the specified brackets 4 constituting the load applying mechanism. Alternatively, a recess between the adjoining surfaces of the teeth 3d, 3e to be aligned and the one between the adjoining surfaces of the teeth 3g, 3h to be aligned shown in FIGS. 1 and 3C may constitute dents 10b' corresponding to the positioning portions.

Figure 3A:
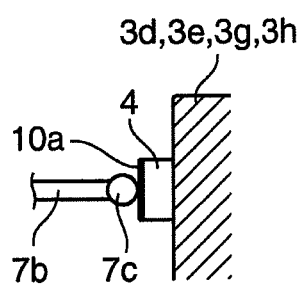
FIGS. 3A, 3B and 3C are sections showing contact states of the load applying mechanism and the vibration generating actuator.
Figure 3B:
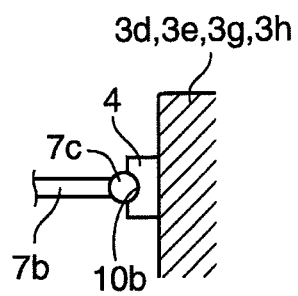
Figure 3C:
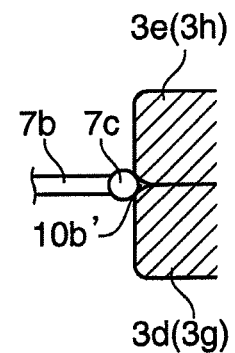

Specifically, if the vibration generating probe 7B shown in FIG. 2B is used as the vibration generating actuator and the positioning portions of the load applying mechanism are the markings (colored markers) 10a shown in FIG. 3A, the ball-shaped vibrating element 7c of the vibration generating probe 7B is inserted into the buccal cavity from the outside, and brought into contact with the bracket 4 using the corresponding marking 10a as a marker. If the positioning portions are the dents 10b shown in FIG. 3B, the ball-shaped vibrating element 7c is brought into contact with the bracket 4 to fit into the corresponding dent 10b. If the positioning portions are the dents (recesses between the adjoining surfaces) 10b' shown in FIG. 3C, the ball-shaped vibrating element 7c is directly brought into contact with the teeth group 3 to fit into the dent 10b'.

Any of the above contacts enables the vibration generating probe 7B to precisely apply vibration only to the teeth 3d, 3e, 3g and 3h to be aligned and their neighboring parts. Such application of the vibration remarkably shortens a period of orthodontic treatment.

Since the load applying mechanism, i.e. the mechanism for applying constant forces to the teeth 3d, 3e, 3g and 3h to be aligned is constructed by a plurality of brackets 4 and the orthodontic wire 5 connecting the brackets 4, it has a low cost.

The above positioning portions, i.e. the markings 10a provided on at least either the brackets 4 or the orthodontic wire 5, the dents 10b, and the dents 10b' formed by the recess between the adjoining surfaces of the teeth 3d, 3e to be aligned and the recess between the adjoining surfaces of the teeth 3g, 3h to be aligned serve as markers upon positioning the vibrating element 7c of the vibration generating probe 7B. Therefore, vibration can be more precisely applied to the teeth 3d, 3e, 3g and 3h to be aligned.

Specifically, the markings 10a as the positioning portions enable the position where the vibrating element 7c of the vibration generating probe 7B should come into contact to be precisely confirmed by the eyes.

Further, since the dents 10b, 10b' as the positioning portions have a function of guiding the vibrating element 7c, the vibrating element 7c and the load applying mechanism or the teeth can be more easily and precisely brought into contact with each other.

A second embodiment of the present invention is shown in FIGS. 4 and 5. A load applying mechanism according to this embodiment is constructed by a dental mouthpiece 9 and projections 15, and this load applying mechanism applies constant forces (static loads) to teeth 3d, 3e, 3g and 3h to be aligned.

Figure 5A:
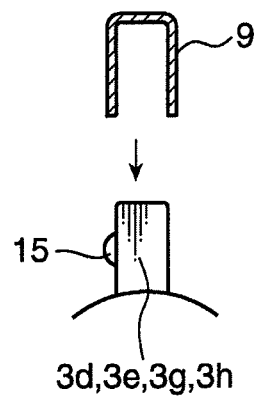
FIGS. 5A and 5B are partial side views in section showing a state before the dental mouthpiece is mounted on teeth and a state where the dental mouthpiece is mounted on the teeth, respectively.
Figure 5B:
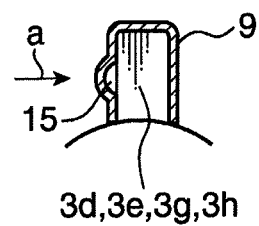

As shown in FIG. 5A, each projection 15 is so fixed to the front surface of a corresponding one of the teeth 3d, 3e, 3g and 3h to be aligned of a teeth group 3 as to project forward. The dental mouthpiece 9 is fitted over these projections 15 as shown in FIGS. 4 and 5B, and forcibly mounted on the teeth group 3. This mounted dental mouthpiece 9 comes to possess contraction forces, which concentrate on the projections 15. The forces concentrated on the projections 15 are applied to the teeth 3d, 3e, 3g and 3h to be aligned as constant forces (arrow "a") for teeth alignment.

A material for ordinary mouthpieces (or mouth guards) and having guaranteed hygienic safety is normally used as the material of the dental mouthpiece 9. The dental mouthpiece 9 is preferably cast into a suitable shape using, for example, an EVA (ethylene vinyl acetate) sheet which is a polymer material. Such a material is preferable since having little side effects on teeth and gingival tissues such as allergy. The material of the dental mouthpiece 9 is suitably selected from soft materials, hard materials or admixtures of soft and hard materials depending on the degree of teeth alignment.

Besides, the mouthpiece 9 can also apply to the teeth a certain force for the orthodontic treatment of the teeth by the inner surface form of the mouthpiece 9 itself. Specifically, it is desirable that the mouthpiece 9 having an inner surface form corresponding to the alignment of the teeth as a final target of an orthodontic treatment or a target in the course of an orthodontic treatment is produced and attached. The mouthpiece 9 having such an inner surface form can apply an appropriate biasing force to the teeth when attached on the teeth.

Markings (colored markers) 10a as positioning portions are applied to parts of the dental mouthpiece 9 corresponding to the teeth 3d, 3e, 3g and 3h to be aligned. The positioning portions are not limited to the markings 10a. For example, instead of the markings 10a, dents 10b shown in FIG. 6B may be formed in the outer surface of the dental mouthpiece 9. Alternatively, as shown in FIGS. 4 and 6C, dents 10b' formed in the outer surface of the dental mouthpiece 9 in correspondence with a recess between the adjoining surfaces of the teeth 3d, 3e to be aligned and a recess between the adjoining surfaces of the teeth 3g, 3h may be respectively used as the positioning portions.

Figure 6A:
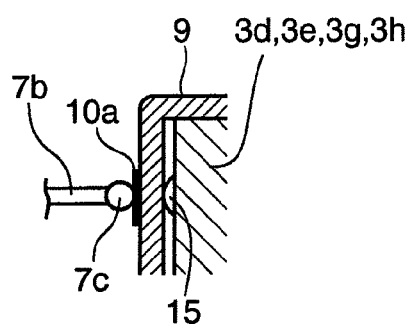
FIGS. 6A, 6B and 6C are sections showing contact states of the dental mouthpiece and a vibration generating actuator.
Figure 6B:
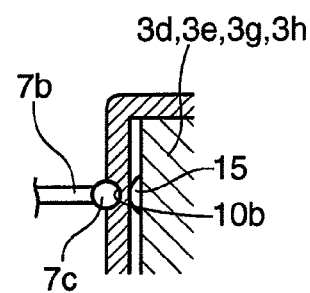
Figure 6C:
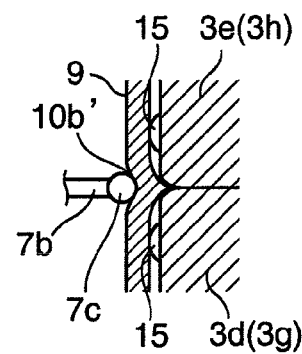
Figure 7A:
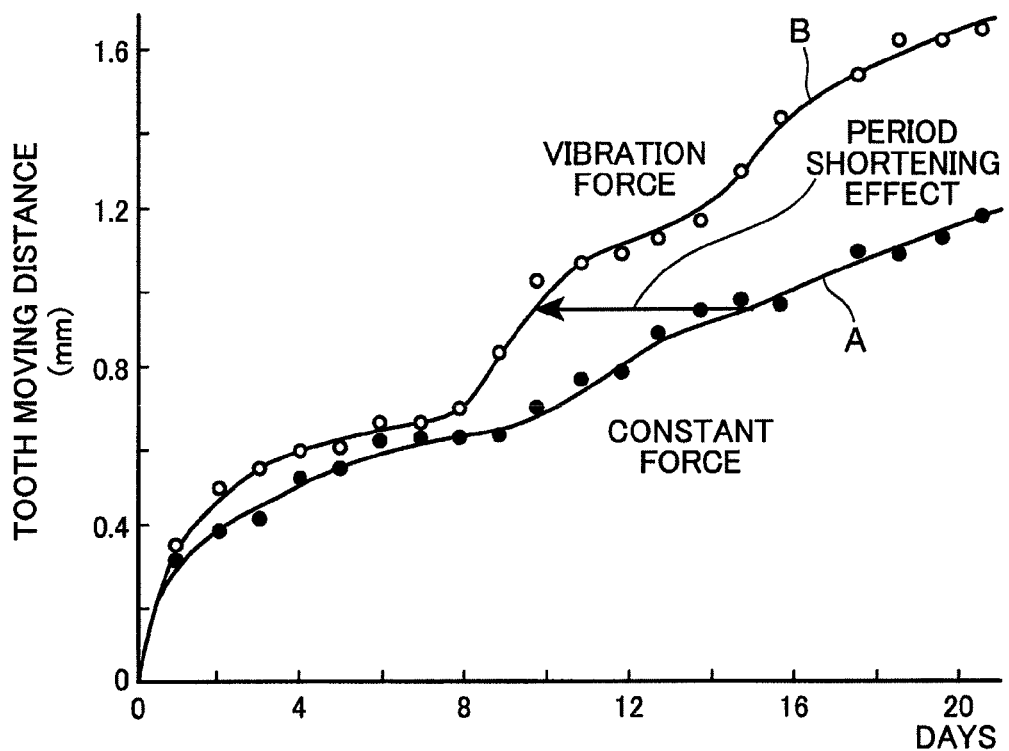
FIGS. 7A and 7B are graphs respectively showing an effect of shortening a period of orthodontic treatment.
Figure 7B:
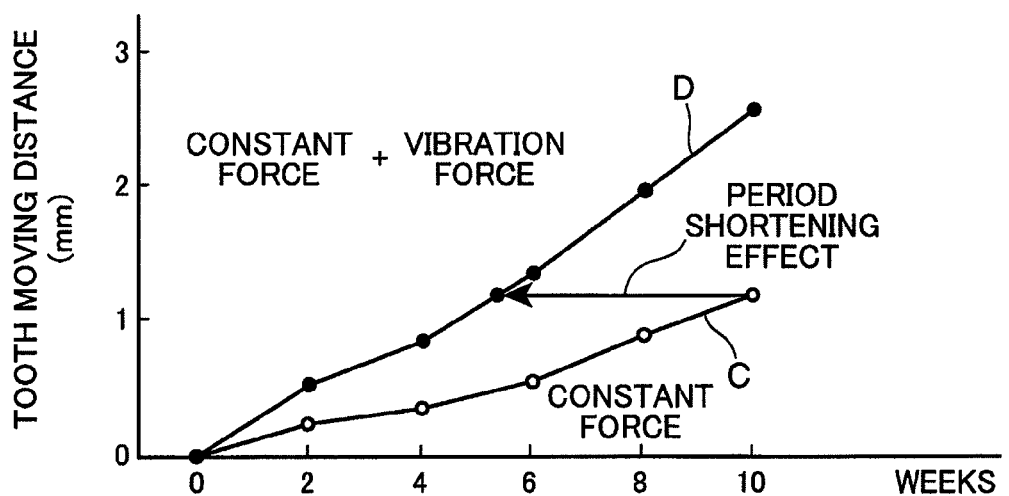

Similar to the first embodiment, if the ball-shaped vibrating element 7c of the vibration generating probe 7B is inserted into the buccal cavity and the markings (colored markers) 10a shown in FIG. 6A constitute the positioning portions, the ball-shaped vibrating element 7c is brought into contact with the marking 10a. If the dents 10b shown in FIG. 6B or the dents 10b' shown in FIG. 6C constitute the positioning portions, the ball-shaped vibrating element 7c is brought into contact with the dental mouthpiece 9 to fit into the dent.

In any of the cases, the ball-shaped vibrating element 7c can be precisely brought into contact with the outer surfaces of parts of the dental mouthpiece 9 corresponding to the teeth 3d, 3e, 3g and 3h to be aligned. This can remarkably shorten a period of orthodontic treatment.

Also, in the case where the dental mouthpiece 9 is used, the bite board 7A shown in FIG. 2A can be used as the vibration generating actuator. In such a case, the main body 20 of the bite board 7A is chewed by the upper and lower teeth via the dental mouthpiece 9. In this way, the main body 20 can be brought into contact with the parts of the dental mouthpiece 9 corresponding to the teeth 3d, 3e, 3g and 3h to be aligned to which constant forces are applied. Thus, vibration can be efficiently applied to the teeth 3d, 3e, 3g and 3h to be aligned. This can remarkably shorten a period of orthodontic treatment.

The dental mouthpiece 9 is forcibly fitted on the teeth group 3 to be placed over the projections 15 fixed to the teeth 3d, 3e, 3g and 3h to be aligned, thereby applying constant forces to the teeth 3d, 3e, 3g and 3h to be aligned. Thus, as compared to the load applying mechanism including the brackets 4 and the orthodontic wire 5, the dental mouthpiece 9 can be easily mounted on and detached from the teeth group 3 to thereby reduce burdens on patients. Further, since the dental mouthpiece 9 shown in FIGS. 4 and 6A to 6C has the markings 10a or the dents 10b, 10b' that are the positioning portions as markers for the contact positions of the vibrating element 7c of the vibration generating probe 7B, vibration can be more precisely applied to the teeth 3d, 3e, 3g and 3h to be aligned.

The positioning portion is not limited to the above-mentioned positioning means for indicating a contact position of the vibrating element 7c to the load applying mechanism including the bracket 4 and the wire 5 or the load applying mechanism including the mouthpiece 9, but may be a positioning means for indicating a contact position of the vibrating element to the teeth. As a positioning portion, for example, it may be appreciated to provide a member extending upward or downward from an appropriate position of the wire 5 and having a shape pointing a contact position to which the vibrating element is to come into contact. Also, the positioning portion may be a through hole which is formed in the mouthpiece 9 and is operable to permit insertion of the vibrating element and guide the vibrating element to the suitable contact position of the teeth.

As described above, an orthodontic appliance according to the present invention comprises a load applying mechanism and a vibration generating actuator. The load applying mechanism is mounted on teeth to apply a load for teeth alignment to a specified tooth in the teeth. The vibration generating actuator includes a contact portion that is inserted into a buccal cavity containing the teeth from the outside and can come into contact with a part of the load applying mechanism corresponding to the specified tooth or the specified tooth, and efficiently applies a vibration force from the contact portion to the specified tooth or the part of the load applying mechanism. This can remarkably shorten a period required for teeth alignment.

The load applying mechanism preferably includes brackets to be fixed to the buccal surfaces of a plurality of teeth in the teeth and an orthodontic wire connecting the brackets, latched by the brackets while being elastically deformed and applying an elastic restoring force thereof to the specified tooth as the load. This mechanism has a simple construction and a low cost.

The load applying mechanism may include a projection fixed to the specified tooth in the teeth to project from the specified tooth and a dental mouthpiece to be mounted on the teeth over the projection, thereby applying a constant force to the tooth to which the projection is fixed. This dental mouthpiece can be easily mounted and detached, which reduces burdens on patients.

The vibration generating actuator preferably includes a main body chewable by upper and lower teeth and a vibrating element built in the main body to generate vibration. This vibration generating actuator can apply vibration to the specified tooth or a part of the load applying mechanism corresponding to the specified tooth only by the main body thereof being chewed by a patient.

The vibration generating actuator may include a vibrating element for generating vibration, and the vibrating element may be so shaped as to be able to come into contact with the part of the load applying mechanism corresponding to the specified tooth or the specified tooth. This vibrating element can efficiently apply vibration to the specified tooth.

The load applying mechanism more preferably includes a positioning portion for determining a position where the vibrating element is supposed to come into contact with the load applying mechanism. This positioning portion helps the vibrating element to more precisely come into contact with the load applying mechanism or a suitable position of the teeth.

The positioning portion is preferably a marking indicating the contact position of the vibrating element or a dent having such a shape that the vibrating element can be fitted into. The latter, i.e. the dent has a function of guiding the vibrating element to the suitable contact position.

What is claim is:

1. An orthodontic appliance for correcting malocclusion, comprising:
   a dental mouthpiece having an inner surface form corresponding to an alignment of teeth as a final target of an orthodontic treatment or a target in a course of an orthodontic treatment to provide an alignment part for applying a biasing force to the specified tooth;
   a load applying mechanism that abuts an inner side surface of the mouthpiece to apply a load for malocclusion correction to a specified tooth;
   a vibrating element adapted for insertion into a buccal cavity containing the teeth from the outside and adapted to apply a vibration force to a part of the mouthpiece; and
   a positioning portion provided on the mouthpiece and for determining a position where the vibrating element is to contact the mouthpiece, the positioning portion comprising a dent formed in the part of the mouthpiece and shaped to conform to the vibrating element such that the vibrating element is removably attached within the dent, the dent being provided in an outer side surface of the mouthpiece at a position corresponding to the specified tooth, and wherein the outer side surface is a facial surface.

* * * * *